United States Patent [19]

von Klock et al.

[11] 4,416,996

[45] Nov. 22, 1983

[54] HYDROGEN BLISTERING CORROSIVITY METERING MEANS AND METHOD

[75] Inventors: Byron von Klock; Dinh-Cuong Vuong, both of Beaumont, Tex.

[73] Assignee: Texaco Inc., White Plains, N.Y.

[21] Appl. No.: 293,720

[22] Filed: Aug. 17, 1981

[51] Int. Cl.³ .............................................. G01N 17/00
[52] U.S. Cl. ............................................ 436/6; 422/53
[58] Field of Search ............................... 436/6; 422/53

[56] References Cited

U.S. PATENT DOCUMENTS

| | | | |
|---|---|---|---|
| 4,020,680 | 5/1977 | Mehizadeh et al. | 422/53 |
| 4,043,178 | 8/1977 | Winslow | 422/53 |
| 4,056,968 | 11/1977 | Winslow | 422/53 |
| 4,065,373 | 12/1977 | Martin | 436/6 |

*Primary Examiner*—Hiram H. Bernstein
*Attorney, Agent, or Firm*—Carl G. Ries; Robert A. Kulason; Ronald G. Gillespie

[57] ABSTRACT

A hydrogen blistering corrosivity meter includes a cavity filled with a monitoring liquid. A liquid to be tested is separated from the monitoring liquid by a steel membrane. A device, which allows the volume of the measuring liquid to be monitored, is connected to the cavity. Dissolved hydrogen atoms, if any, formed by the test liquid diffuse through the steel membrane and enter the cavity, forming molecular hydrogen and causing an increase in volume in the measuring liquid which corresponds to the rate of corrosion activity.

24 Claims, 6 Drawing Figures

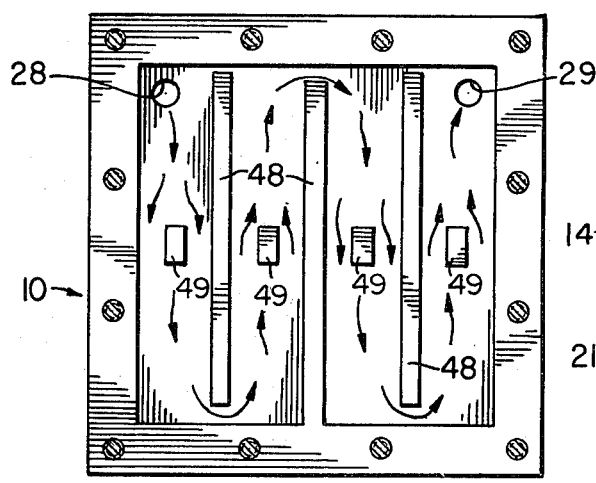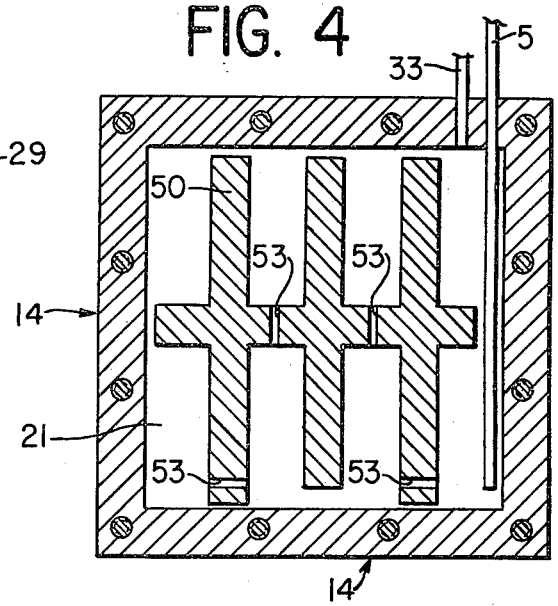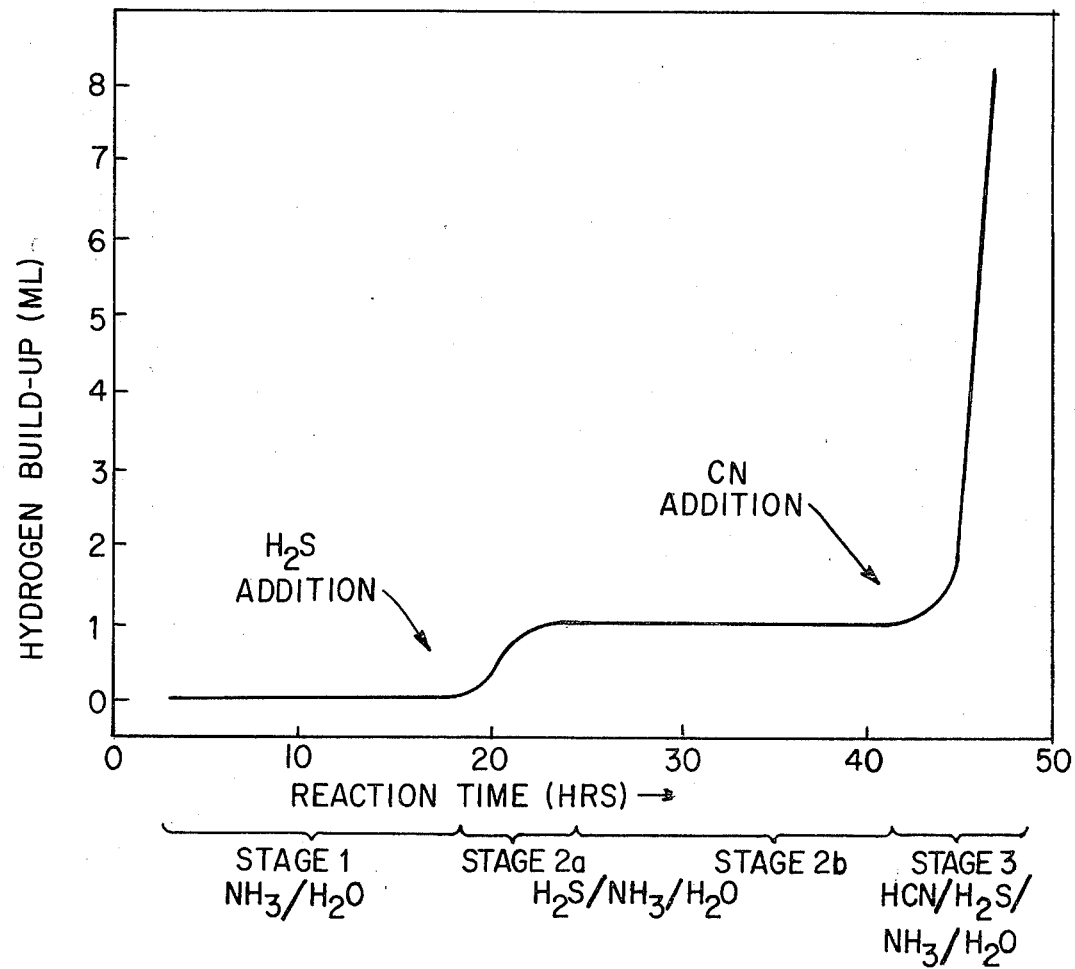

HYDROGEN BLISTERING CORROSIVITY METERING MEANS AND METHOD

BACKGROUND OF THE INVENTION

Field of the Invention

The present invention relates to meters and metering methods in general and, more particularly, to hydrogen blistering meters and metering methods.

SUMMARY OF THE INVENTION

A hydrogen blistering corrosivity meter includes a cavity containing a measuring liquid. A liquid being tested is separated from the measuring liquid by a steel membrane. A device is connected to the cavity which allows the volume of the measuring liquid to be monitored. Dissolved hydrogen atoms, if any, formed by the test liquid diffuse through the steel membrane and enter the cavity, forming molecular hydrogen and causing an increase in the volume of the measuring liquid which corresponds to the rate of corrosion activity.

The objects and advantages of the invention will appear more fully hereinafter from a consideration of the detailed description which follows, taken together with the accompanying drawings wherein one embodiment of the invention is illustrated by way of example. It is to be expressly understood, however, that the drawings are for illustration purposes only and are not to be construed as defining the limits of the invention.

DESCRIPTION OF THE DRAWINGS

FIGS. 3 and 4 show the end plate and center plate of the test cell shown in FIG. 1.

FIG. 5 is a graph of hydrogen buildup vs. reaction time depicting test results of the hydrogen blistering corrosivity meter constructed in accordance with the present invention.

DESCRIPTION OF THE INVENTION

Figure 1:
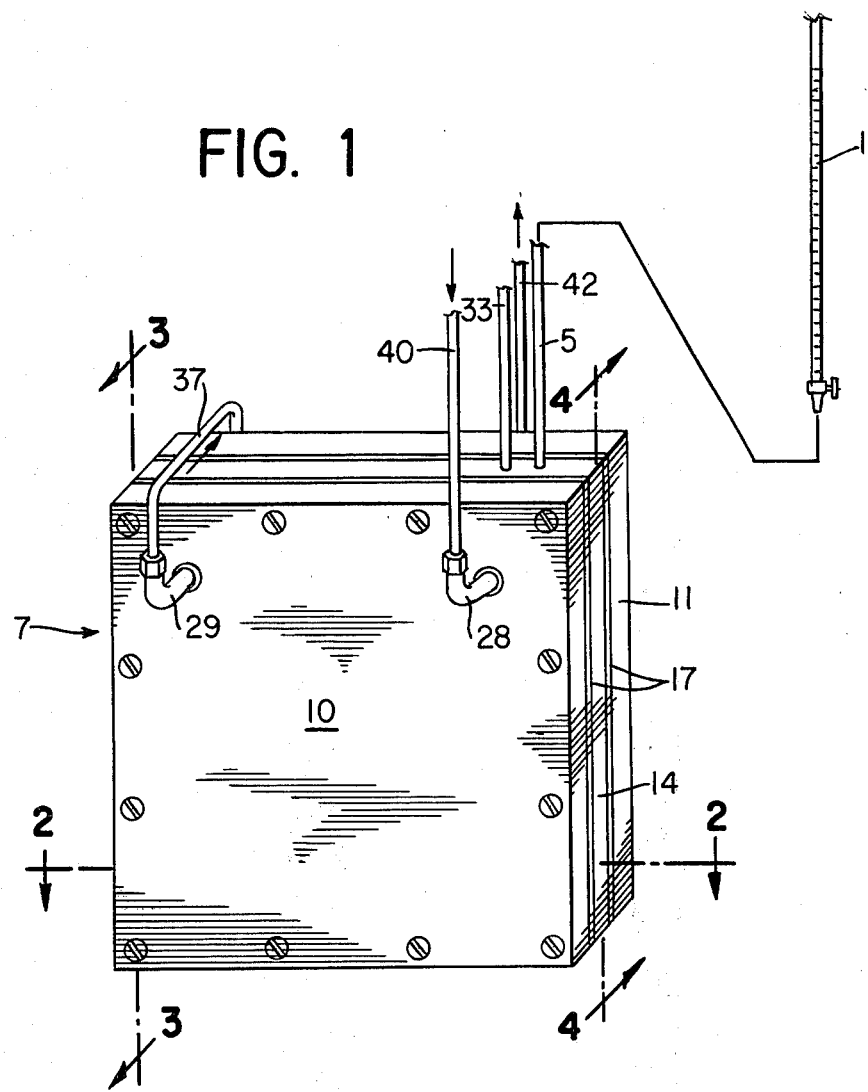
FIG. 1 is a pictorial drawing of a hydrogen blistering corrosivity meter constructed in accordance with the present invention.

A problem which is of increasingly serious concern to the petroleum industry as heavier crudes with higher sulfur and nitrogen contents are processed, is cyanide-promoted sour water hydrogen blistering corrosion, which occurs mostly in the recovery section of fluidized catalytic cracking units. Catalytic crackers and hydrogenation units convert a fraction of the charge stock nitrogen to hydrogen cyanide, which dissolves, along with hydrogen sulfide and ammonia, in the recovery section sour water condensate; typical concentrations are 100 mg/L HCN, 6000 mg/L $H_2S$ and 4000 mg/L $NH_3$.

Hydrogen blistering occurs when the protective iron sulfide deposit which forms on steel surfaces in the sulfidic environment is dissolved by cyanide attack:

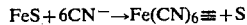

The exposed steel surface is attacked by hydrogen sulfide, forming hydrogen atoms which dissolve in steel:

The dissolved hydrogen atoms diffuse through the steel until an imperfection in the metal is reached; at this point the hydrogen atoms combine to make molecular hydrogen gas:

Hydrogen gas is not soluble in steel, so the process is unidirectional; hydrogen gas accumulates in the cavity until pressures of several hundred thousand psi are reached. At this time the steel plate deforms and the cavity becomes a hydrogen blister. Eventually, the blister ruptures, reducing the thickness of the steel plate at that point to a fraction of its original thickness. The process is harmful, not only because of the expense of filling or replacing a thick steel vessel wall, but also because a complete rupture in a high-pressure naphtha processing vessel could easily lead to a devastating explosion and fire.

There are existing methods of measuring sour water hydrogen-blistering corrosivity, but all have disadvantages which the present invention avoids. Conventional type corrosion coupons cannot be used in the normal manner since hydrogen blistering is not a weight-loss process. Blisters will form in a steel coupon, but corrosivity determination by blister-counting is at best only semi-quantitative. Hydrogen probes, which measure the buildup of hydrogen pressure in a small void volume inside a steel shell which is immersed in the sour water, are fairly widely used on process units. Their main disadvantage is slow response, since several weeks may be required to detect a significant pressure change. They are also prone to failure due to undetectable minute leaks at welds or pressure gauge screw threads, which leads to dangerously misleading false negative readings. Hydrogen patches are plates with pressure gauges which are welded to the outside of process vessels; they operate in the same manner as and have the same disadvantages as hydrogen probes. A third method measures hydrogen penetration through a steel membrane by electro-chemical means; the disadvantages of this are expense, complexity (making malfunction more probable), and fragility (for use in field work).

The present invention utilizes direct volumetric measurement of hydrogen penetration through a steel membrane in contact with the sour water.

Figure 2:
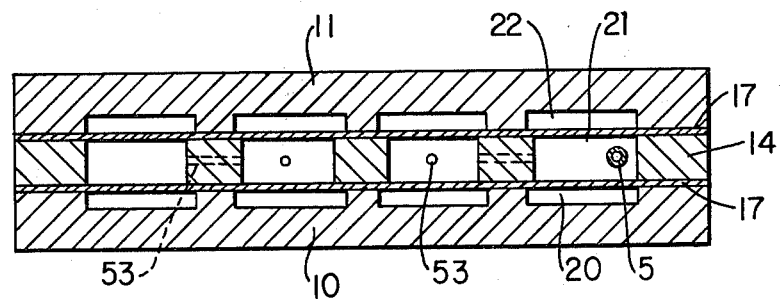
FIG. 2 is a cross-sectional view of the test cell shown in FIG. 1 along the line 2—2 in the direction of the arrows.

Referring now to FIG. 1, there is shown a volumetric hydrogen blistering corrosivity meter having a graduated glass burette 1 connected to an outlet line 5 of a test cell 7. FIG. 2 is a cutaway view of test cell 7 along the lines 2—2 while FIG. 3 and FIG. 4 show the details of the end plates 10, 11 and a center plate 14, respectively.

When assembled as shown, steel membranes 17 separate end plates 10 and 11 from center plate 14 to form three cavities 20, 21 and 22. End plates 10, 11 and center plate 14 may be made from any rigid material which will not be corroded by the test fluid or the measuring fluid. One such material is polycarbonate plastic.

End plates 10, 11 have inlet and outlet fittings which on end plate 10 are identified as inlet fitting 28 and outlet fitting 29. Center plate 14 has a fill line 33 and outlet line 5 connected to the burette 1. Outlet fitting 29 of end plate 10 is connected to the input fitting (not shown) of end plate 11 by a tube 37. The inlet fitting 28 of end plate 10 is connected to an inlet line 40 connected to the processing system in which the sour water is to be monitored while an outlet tubing 42 is connected to the outlet fitting (not shown) of end plate 11, and goes to a drain (not shown).

End plates 10 and 11 further have flow direction baffles 48 to assure an optimum flow path, and membrane support bosses 49, to assist in keeping the membranes rigid.

A membrane supporter 50, made from the same material as end plates 10, 11 and center plate 14, is removable and has gas bleed holes 53. Membrane supporter 50 is used in conjunction with center plate 14 to support membranes 17.

In operation a liquid is injected through fill tube 33 until it fills cavity 21 and continues through outlet line 5 to graduated burette 1 until a discernible reading is obtained. Then the fill tube 33 is closed off and sour water, or a liquid to be monitored, passes through tube 40 into cavity 20 through fitting 28, passes back and forth across a first membrane 17 through cavity 20 to fitting 29, through tube 37 and an inlet fitting (not shown) into cavity 22, passes back and forth across a second membrane 17 through cavity 22 to its outlet fitting (not shown) and through tube 42 to the drain (not shown). The dissolved hydrogen atoms resulting from the chemistry as hereinbefore explained diffuse through steel membranes 17 and enter inner cavity 21, where they combine to form molecular hydrogen gas, displacing a corresponding volume of liquid. Since inner cavity 21 represents a constant volume the only volume change that will occur is that of the liquid in graduated glass burette 1. The change in volume is then monitored and recorded as necessary.

Referring now to FIG. 5, in a test of the present invention three stages were developed. In stage 1, diluted ammonia solution was passed through cavities 20 and 22 but did not react with steel membranes 17 and no hydrogen was formed. In stage 2, hydrogen sulfide was added. During the first portion of stage 2, shown as 2a, the hydrogen sulfide reacted with the fresh steel surface to generate hydrogen resulting in the increase in hydrogen buildup in burette 1. However, the hydrogen sulfide also reacted with steel membranes 17 to form black FeS scale on the steel surfaces 17 which eventually retarded the corrosive reaction and protected steel membranes 17. Thus, during the latter portion of stage 2, shown as 2b, no more hydrogen was formed. In stage 3, cyanide was added which resulted in severe corrosion and rapid hydrogen evolution. With only 300 mg/L cyanide in the sour water, approximately 5 ml/hr hydrogen was collected. This is equivalent to 0.503 ml/cm$^2$-day hydrogen penetration, which indicates a severe corrosion situation.

Figure 6:
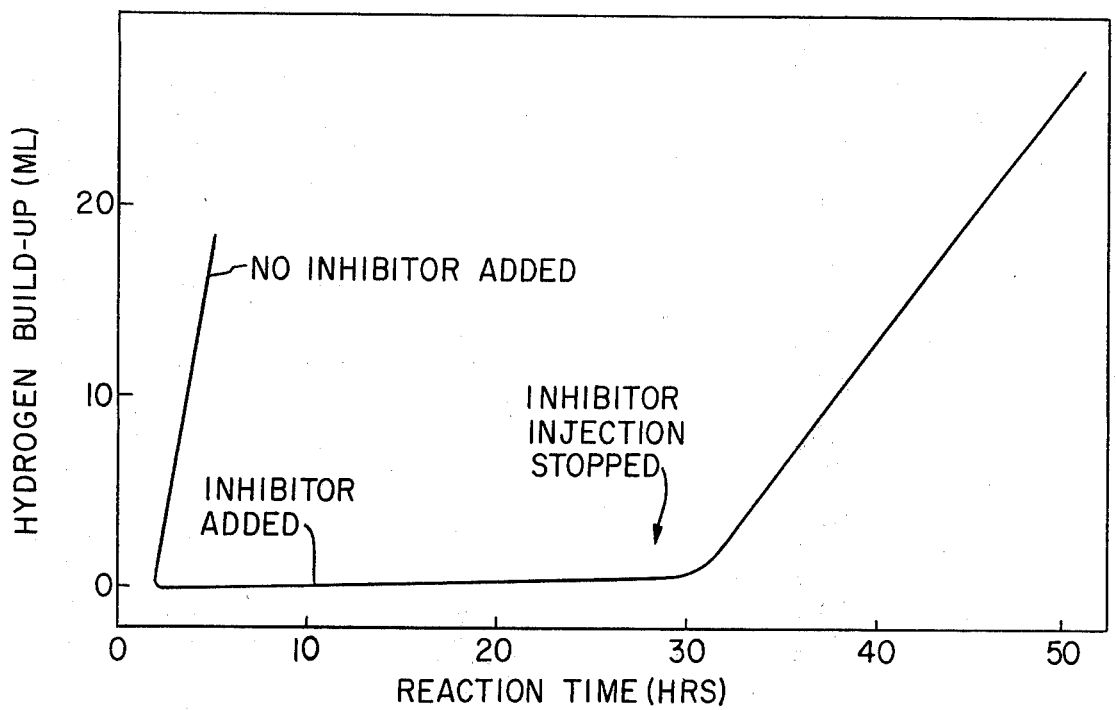
FIG. 6 is a graphical representation of hydrogen buildup vs. reaction time illustrating the effect of a corrosion inhibitor.

FIG. 6 also demonstrates that the present invention may be used as a corrosion inhibitor monitor. Sour water with no corrosion inhibitor added was tested with the present invention. The same sour water with a corrosion inhibitor being injected showed the reduction of the hydrogen blistering corrosion activity until such time as the corrosion inhibitor injection was stopped. For awhile thereafter, the corrosion inhibitor effect was still present, but in time the corrosion inhibitor was desorbed from the steel membranes 17 and the sour water continued to corrode steel membranes 17.

The present invention as hereinbefore described is a volumetric hydrogen blistering corrosivity meter in which a known volume is created with steel membranes and the change in volume is measured as the effect of the corrosive activity of sour water.

What is claimed is:

1. A method of monitoring hydrogen blistering corrosivity comprising
    containing a predetermined volume of measuring liquid in a container having at least one steel membrane as a side,
    contacting a liquid to be tested with the steel membrane in a manner so that hydrogen atoms formed by the corrosive activity of the test liquid with the steel membrane passes through the steel membrane to the measuring liquid, and
    measuring a change in the volume of the measuring liquid resulting from the corrosive activity of the test liquid with the steel membrane.

2. A method as described in claim 1 in which the measuring step includes
    containing a portion of the predetermined volume of the measuring liquid in a burette in a manner so that as the volume of the measuring liquid changes, the portion of the measuring liquid in the burette changes accordingly.

3. A method of monitoring hydrogen blistering corrosivity comprising the steps of
    providing first, second and third cavities,
    separating the cavities with steel membranes so that a first steel membrane separates said second cavity from said first cavity and a second steel membrane means separates said second cavity from said third cavity,
    containing a predetermined volume of a measuring liquid in said second cavity,
    passing a liquid to be tested through said first and third cavities in a manner so that it comes in contact with the first and second steel membranes, and
    measuring a change in the volume of the measuring liquid resulting from the passage through the steel membranes of hydrogen atoms formed by the corrosive activity of the test liquid with the steel membrane means.

4. A method as described in claim 3 in which the measuring step includes
    containing a portion of the predetermined volume of measuring liquid in a burette connected to the second cavity in a manner so that a change in volume of the measuring liquid occurs in the burette.

5. A hydrogen blistering corrosivity meter comprising
    means for containing a predetermined volume of measuring liquid,
    steel membrane means spatially related to the containing means,
    means for contacting a liquid to be tested with the steel membrane means in a manner so that hydrogen atoms formed by the corrosive activity of the test liquid with the steel membrane means passes through the steel membrane means to the measuring liquid, and
    means for measuring a change in the volume of the measuring liquid resulting from the corrosive activity of the test liquid with the steel membrane.

6. A corrosivity meter as described in claim 5 in which the measuring means includes
    a burette connected to the containing means in a manner so that a portion of the predetermined volume of measuring liquid is also contained in the burette so that as the volume of the measuring liquid changes, the portion of the measuring liquid in the burette changes accordingly.

7. A hydrogen blistering corrosivity meter comprising housing means including
first, second and third cavities, and
first and second steel membrane means, said first steel membrane means separating the second cavity from the first cavity and said second steel membrane means separating said second cavity from said third cavity;
a predetermined volume of a measuring liquid contained in said second cavity;
means for passing a liquid to be tested through said first and third cavities in a manner so that the test liquid comes in contact with the first and second steel membranes; and
means for measuring change in the volume of the measuring liquid resulting from the passage through the steel membranes of hydrogen atoms formed by the corrosive activity of the test liquid with the steel membrane means.

8. A corrosivity meter as described in claim 7 in which the measuring means includes
a burette connected to the second cavity and the predetermined volume of measuring liquid is contained in the second cavity and the burette so that a change in volume of the measuring liquid occurs in the burette.

9. A corrosivity meter as described in claim 8 in which the housing means includes
two end plate means, one end plate means includes an entranceway for the test liquid to enter the first cavity while the other end plate means includes an exitway for the test liquid to exit the third cavity,
center plate means affixed together in such a manner so that the center plate means is separated from each end plate means by a steel membrane to form the three cavities, and the center plate means includes an exitway connected to the burette and fill means for filling the second cavity and a portion of the burette with the predetermined volume of measuring liquid, and
pipe means for conveying the test liquid from the first cavity to the third cavity.

10. A corrosivity meter as described in claim 9 in which each end plate means includes baffle means for directing the flow of the test liquid so as to enhance its contact with the steel membranes, and support means for supporting the steel membranes.

11. A corrosivity meter as described in claim 10 in which the center plate means includes support means for supporting the steel membranes.

12. A corrosivity meter as described in claim 11 in which the support means in the center plate means has bleed holes for the passage of hydrogen.

13. A method of monitoring the effectiveness of a hydrogen blistering corrosion inhibitor comprising
containing a predetermined volume of measuring liquid in a container having at least one steel membrane as a side,
contacting a test liquid, containing the corrosion inhibitor to be tested, with the steel membrane in a manner so that hydrogen atoms formed by the corrosive activity of the test liquid with the steel membrane passes through the steel membrane to the measuring liquid, and
measuring a change in the volume of the measuring liquid resulting from the corrosive activity of the test liquid with the steel membrane over a period of time so as to monitor the effectiveness of the corrosion inhibitor.

14. A method as described in claim 13 in which the test liquid without the corrosion inhibitor is a predetermined corrosive liquid.

15. A method as described in claim 14 in which the measuring step includes
containing a portion of the predetermined volume of the measuring liquid in a burette in a manner so that as the volume of the measuring liquid changes, the portion of the measuring liquid in the burette changes accordingly.

16. A method of monitoring hydrogen blistering corrosivity comprising the steps of
providing first, second and third cavities,
separating the cavities with steel membranes so that a first steel membrane separates said second cavity from said first cavity and a second steel membrane means separates said second cavity from said third cavity,
containing a predetermined volume of a measuring liquid in said second cavity,
passing a test liquid, containing the corrosion inhibitor to be tested, through said first and third cavities in a manner so that it comes in contact with the first and second steel membranes, and
measuring a change in the volume of the measuring liquid, resulting from the passage through the steel membranes of hydrogen atoms formed by the corrosive activity of the test liquid with the steel membrane means, over a period of time so as to monitor the effectiveness of the corrosion inhibitor.

17. A method as described in claim 16 in which the measuring step includes
containing a portion of the predetermined volume of measuring liquid in a burette connected to the second cavity in a manner so that a change in volume of the measuring liquid occurs in the burette.

18. A corrosion inhibitor monitor comprising
means for containing a predetermined volume of measuring liquid,
steel membrane means spatially related to the containing means,
means for contacting a test liquid, containing a corrosion inhibitor to be tested, with the steel membrane means in a manner so that hydrogen atoms formed by the corrosive activity of the test liquid with the steel membrane means passes through the steel membrane means to the measuring liquid, and
means for measuring a change in the volume of the measuring liquid resulting from corrosive activity of the test liquid with the steel membrane so as to monitor the effectiveness of the corrosion inhibitor.

19. A monitor as described in claim 18 in which the test liquid without the corrosion inhibitor is a predetermined corrosive liquid.

20. A corrosivity meter as described in claim 19 in which the measuring means includes
a burette connected to the containing means in a manner so that a portion of the predetermined volume of measuring liquid is also contained in the burette so that as the volume of the measuring liquid changes, the portion of the measuring liquid in the burette changes accordingly.

21. A corrosion inhibitor monitor comprising housing means including
   first, second and third cavities, and
   first and second steel membrane means, said first steel membrane means separating the second cavity from the first cavity and said second steel membrane means separating said second cavity from said third cavity;
   a predetermined volume of a measuring liquid contained in said second cavity;
   means for passing a test liquid, containing a corrosion inhibitor to be tested, through said first and third cavities in a manner so that the test liquid comes in contact with the first and second steel membranes, and
   means for measuring change in the volume of the measuring liquid resulting from the passage through the steel membranes of hydrogen atoms formed by the corrosive activity of the test liquid with the steel membrane means.

22. A monitor as described in claim 21 in which the test liquid without the corrosion inhibitor is a predetermined corrosive liquid.

23. A corrosivity meter as described in claim 22 in which the measuring means includes
   a burette connected to the second cavity and the predetermined volume of measuring liquid is contained in the second cavity and in the burette so that a change in volume of the measuring liquid occurs in the burette.

24. A corrosivity meter as described in claim 23 in which the housing means includes
   two end plate means, one end plate includes an entranceway for the test liquid to enter the first cavity while the other end plate means includes an exitway for the test liquid to exit the third cavity,
   center plate means affixed together in such a manner so that the center plate means is separated from each end plate means by a steel membrane to form the three cavities, and the center plate means includes an exitway connected to the burette and a fill means for filling the second cavity and a portion of the burette with the predetermined volume of measuring liquid, and
   pipe means conveys the test liquid from the first cavity to the third cavity.

* * * * *